(12) United States Patent
Pawlowski et al.

(10) Patent No.: US 6,942,656 B2
(45) Date of Patent: Sep. 13, 2005

(54) METHOD FOR ACCURATE OPTICAL TREATMENT OF AN EYE'S FUNDUS

(75) Inventors: Dirk Pawlowski, Jena (DE); Wolfgang Neuberger, Labuan (MY)

(73) Assignee: CeramOptec Industries, Inc., East Longmeadow, MA (US)

( * ) Notice: Subject to any disclaimer, the term of this patent is extended or adjusted under 35 U.S.C. 154(b) by 216 days.

(21) Appl. No.: 10/208,218

(22) Filed: Jul. 30, 2002

(65) Prior Publication Data

US 2003/0009155 A1 Jan. 9, 2003

Related U.S. Application Data

(62) Division of application No. 09/569,438, filed on May 12, 2000, now Pat. No. 6,494,878.

(51) Int. Cl.[7] .............................................. A61B 18/18
(52) U.S. Cl. .......................................... 606/4; 128/898
(58) Field of Search ......................... 128/898; 606/1–6, 606/10–13; 607/88

(56) References Cited

U.S. PATENT DOCUMENTS 5,336,216 A    8/1994  Dewey
6,128,524 A  * 10/2000  Yoneya et al. ............... 600/431
6,494,878 B1 * 12/2002  Pawlowski et al. ............ 606/4

* cited by examiner

Primary Examiner—Michael Peffley
Assistant Examiner—Pete Vrettakos
(74) Attorney, Agent, or Firm—Bolesh J. Skutnik; B J Associates

(57) ABSTRACT

A system and method is provided to accurately treat sites on an eye's retina employing computer based image generation, processing and central control means in conjunction with diode laser sources and optical fibers. The system and method accurately determine geometry of a treatment zone of a specific eye's fundus and adjust a treatment beam to irradiate the treatment zone with minimal coverage of adjacent well tissue. The treatment zone or zone is accurately determined with digital processing of angiographic data and slit lamp image data. This information is integrated with information on the treatment beam characteristics to better match treatment beam coverage with minimal overlap with healthy areas of the fundus. Additionally preferred embodiments also have the ability to automatically track eye movement and switch the beam source depending on eye movement, adjusting the beam spot area in real time.

13 Claims, 7 Drawing Sheets

METHOD FOR ACCURATE OPTICAL TREATMENT OF AN EYE'S FUNDUS

REFERENCE TO RELATED CASE

This application is a divisional of U.S. patent application Ser. No. 09/569,438 filed on May 12, 2000, now U.S. Pat. No. 6,494,878 by Dirk Pawlowski and Wolfgang Neuberger, inventors, entitled "SYSTEM AND METHOD FOR ACCURATE OPTICAL TREATMENT OF AN EYE'S FUNDUS".

BACKGROUND OF THE INVENTION

1. Field of the Invention

The invention relates to the field of ophthalmology, in particular to the field of optical treatment of an eye's fundus using lasers. More specifically it deals with the application of computer based image generation, processing and central control means to accurately treat sites on an eye's retina, particularly its macula in connection with diode laser sources and optical fibers.

2. Information Disclosure Statement

Laser methods are widely accepted in today's modern ophthalmology, as well as in pure diagnosis like laser scanning ophthalmoscopes for the treatment of an eye. Treatment methods include laser reshaping of the cornea to correct strong myopic or presbyopic effects, laser surgery in the eye itself and several treatments of the retina. Retina related methods include coagulation laser systems and, more recently, PhotoDynamic Therapy (PDT) treatments of the retina. For example coagulation laser treatment can be used to re-weld the retina to the eye background if the retina tends to loosen from the eye background, which can lead to complete blindness. Another kind of therapy is to stop the so called age related macula degeneration (AMD). This disease is characterized by untypical blood agglomeration in the macula, the part of highest vision sensitivity of the retina. These blood agglomerations do still circulate, hence it is possible to make an accurate diagnosis applying the so called fluorescence angiography. A certain fluorescing drug is added to the patient's blood circuit and then an image of the retina is taken. The fluorescing drug allows the exact visualization of all blood vessels on the retina and thus in particular those being responsible for the age related macula degeneration. This degeneration actually can not be reversed, but it can be stopped hence the complete loss of eyesight can be prevented.

A recent method is based on so called PDT means. In this treatment, a PDT drug is introduced into the patients blood circulation. The drug is originally harmless and has usually no therapeutic effects, but it is sensitive to illumination at a certain wavelength. If light of this suitable wavelength is absorbed by the drug molecules, they undergo a chemical reaction to another product, which is responsible for the therapeutic effect. In a simple case, this effect is the excitation of the drug molecule to an excited state where it can react with oxygen to form singlet oxygen which is highly reactive. The singlet oxygen quickly reacts with nearby tissue to oxidize it, i.e. cause necrosis. Alternatively, the splitting of one molecule can create two radicals, which are chemically very reactive and can destroy body cells. Because this method is very selective, it widely prevents negative side effects of the therapy by only illuminating the infected area Typical applications apart from the therapy of the age related macula include tumor treatments, are catheter disinfection and dermatological applications. Concerning the treatment of age related macula degeneration, recently the described simple PDT method has been applied. The drug was given to the patient and after a certain time the macula was illuminated with the beam spot of light at the critical wavelength, preferably provided by a laser or a fiber coupled diode laser. Blood agglomeration vessels are then destroyed by the generated therapeutic substance and the age related macula degeneration is stopped. In U.S. Pat. No. 5,336,216 [D. A. Dewey] a method for generating a treatment beam spot on the retina is claimed, which in particular generates a spot on the retina which has a rect-angular intensity profile, also known as top-hat profile for all sizes. This method suffers from the fact, that the knowledge about the treatment zone is only rudimentary. As described in the latter the treatment can be significantly enhanced if the treatment zone is well known.

As noted above, laser based methods of fundus treatment is widely accepted in today's ophthalmology and applied in different forms. For several forms of the treatments focused laser beams are used, as for example in laser abrasive cornea treatment in order to correct myopic or presbyopic defects. Further, laser coagulation routines are performed, in order to re-weld the retina to the eye background, if it becomes unbound, which would result in complete blindness. PDT treatment is a relatively novel method to heal certain diseases of the eye. Especially successful it can be used for the correction of the so called AMD, where certain defects of the blood vessels in the macula can cause the macula to loose from the eye background. The photodynamic substances are introduced to the patients blood circuit and the treatment zone is irradiated with light of a suitable wavelength in order to start a localized treatment effect only in the region of the treatment zone. Several disadvantages are associated with the state of the art in today's PDT methods. The most striking is the strong inaccuracy of the process can be attributed to the lack of means for an accurate determination of the treatment zone and therefore the lack of beam area generating devices providing the desired accuracy.

However, the state of the art illumination means are designed such, that it is impossible to obtain an illumination of the treatment zone alone. The operator has to calculate from fluorescence angiographic diagnostics how large the treatment area is, and then manually adjust the laser beam spot size to be large enough to completely cover the treatment area. This method is extremely inaccurate since no information about the specific eye is provided therein. The spot size on the retina varies with different patient's different eyeballs, but the justification is absolute. This problem is addressed by the present invention.

Since the typically used slit-lamp generated pictures are only of medium quality the treatment zone can be hardly noticeable therein. Hence it's size must be determined from the fluorescence angiography, but this image does not have any relation to the images generated by the slit lamp, though it is the same eyeball, for reasons of different optics, different viewing angles and so on. In any case, whether the treatment is determined from the slit lamp picture or from the angiography, the error made by the calculation of the beam spot size is significant and typically exceeds 200%.

For this reason it is obvious, that not only the treatment zone is illuminated, but also the healthy zones in the eye. This can lead to the destruction of important blood vessels followed by a reduction of eyesight. The present invention provides a solution to this.

State of the art methods apply a treatment beam source which generates a round intensity profile, this intensity profile is either of a gaussian or near gaussian shape or of a so called top hat structure which is characterized by a very sharp edged rise and fall of the intensity at the edges and a near constant intensity in the middle. In any case, the created variable spot size is of a round shape. Obviously, the shape of the treatment zone is not necessarily round. In the most simple case, it has an oval or a slit form, but typically the shape of the area needing treatment is of a more complicated structure. Since, in state of the art devices and methods to perform fundus treatments, there is a very large error in treatment areas anyway, there has been no need for generating a better overlap of the treatment zone and the treatment beam spot area. This is addressed in the present invention now that the treatment beam is more accurately formed and projected onto the treatment zone.

A general problem in laser based fundus treatment is the movement of the eyeball during the treatment. From clinical studies the optimal illumination times are known, but during treatment it must be assured that the treatment zone is illuminated for this period. State of the art solutions operated with an real time viewing by the operator by means of a fundus viewing ocular. The device further provides means for the operator to switch the treatment beam source on an off and thus to control the beam source such, that the illumination is only working, if the treatment zone is within a certain region. This method is a potential source of inaccuracy, because both, the beam and the treatment zone are barely visible during the treatment. The present invention provides a solution to this and the several problems identified above.

OBJECTS AND SUMMARY OF THE INVENTION

It is an object of the invention to provide a method of accurately adjusting the laser beam spot size to the treatment area for each specific eyeball.

It is another object of the invention to determine the exactly the size of the treatment zone from a digital processing of angiography and slit lamp image.

It is yet another object of the invention, to provide an device to achieve significantly better overlap of the treatment zone and the treatment beam spot area.

It is further an object of the invention to provide an device allowing an accurate viewing and means for automatic switching of the beam source depending on the eye movement as well as a device capable of adjusting the spot area in real time according to the eye movement.

Briefly stated, the present invention provides a system and method to accurately treat sites on an eye's retina employing computer based image generation, processing and central control means in conjunction with diode laser sources and optical fibers. The system and method accurately determine geometry of a treatment zone of a specific eye's fundus and adjust a treatment beam to irradiate the treatment zone with minimal coverage of adjacent well tissue. The treatment zone or zone is accurately determined with digital processing of angiographic data and slit lamp image data This information is integrated with information on the treatment beam characteristics to better match treatment beam coverage with minimal overlap with healthy areas of the fundus. Additionally preferred embodiments also have the ability to automatically track eye movement and switch the beam source depending on eye movement, adjusting the beam spot area in real time.

The above, and other objects, features and advantages of the present invention will become apparent from the following description read in conjunction with the accompanying drawings, in which like reference numbers in different drawings denote like items.

DETAILED DESCRIPTION OF PREFERRED EMBODIMENTS

The accuracy of the treatment of the fundus of an eye can be drastically enhanced by the combination of diagnostic means with a therapeutic setup. The therapeutic setup consists of a light source, preferably a fiber coupled diode laser and a suitable optical systems which allows one to vary the spot size generated on the retina. The diagnostic device is preferably a slit lamp with an additional optical setup to allow direct fundus viewing through an eyepiece and simultaneously the generation of a digital image of the fundus. The digital image of the fundus is grabbed by a computer based image processor and an image generation device, preferably a CCD camera. From this image the size of the treatment zone can be determined and electronically processed. The treatment beam spot area is variable and a digital image of the fundus is generated with the a simulation of the treatment beam at a fixed position of the treatment beam spot area varying optical system. From these two images it is possible to adjust the treatment beam spot area to the actual treatment zone size.

Further, if the treatment zone is not sufficiently clearly definable in the generated diagnostic image, it is a subject of the invention to include a digital image generated by means of fluorescence angiography, align this image which is characterized by an extremely high quality to the image obtained by the diagnostic means in the claimed treatment device and determine the necessary treatment beam spot size from the treatment zone area that is visible in the image obtained by fluorescence angiography.

All points mentioned can be either implemented in an automatic way or require manual settings by the operator, or be realized in a combination. Several methods to generate a variable beam spot area on the retina are also subjects of the invention.

Figure 1:
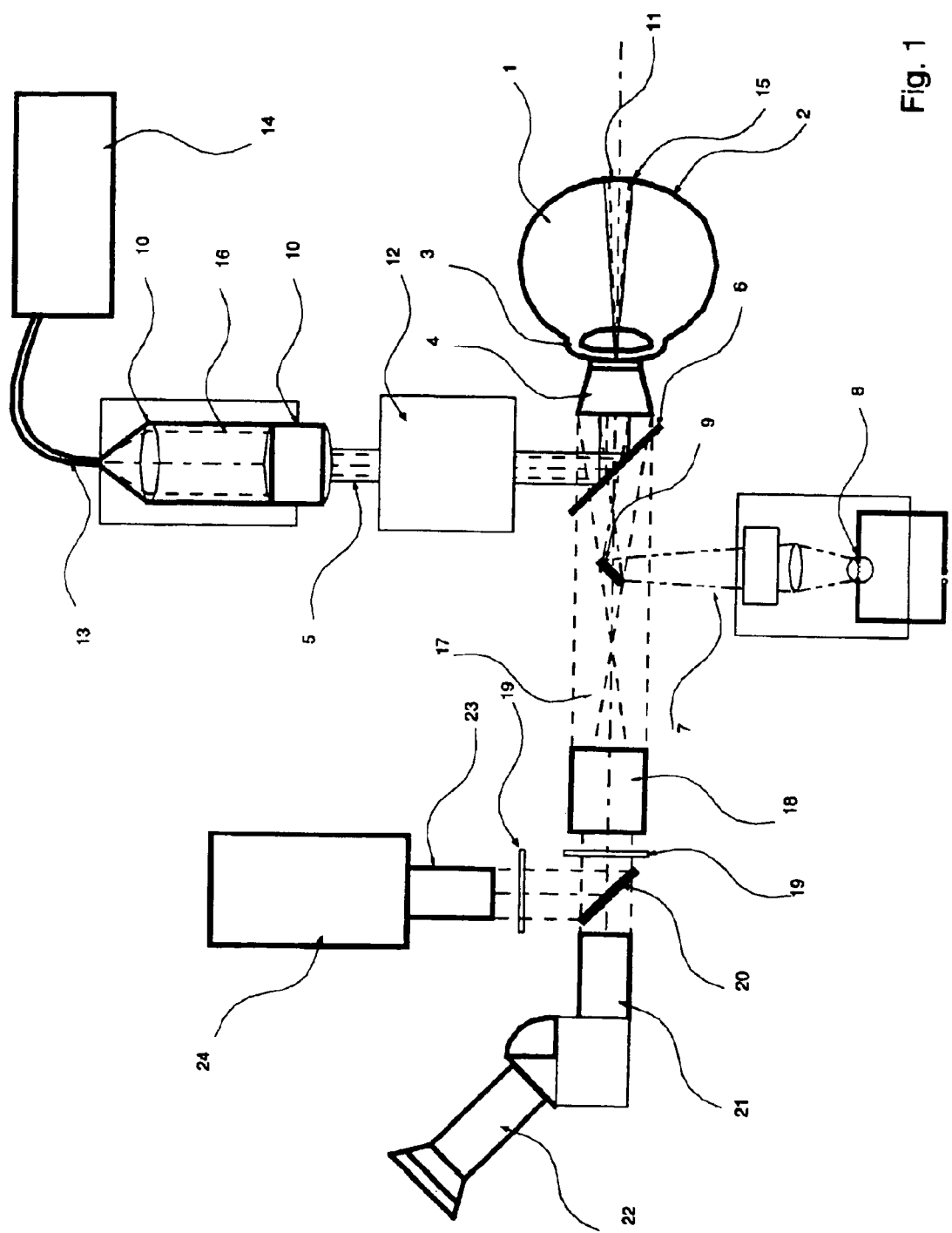
FIG. 1 illustrates the general setup of a device for treatment of an eye's fundus.

FIG. 1 illustrates the setup of the whole device with all elements that are necessary to perform treatments of age related macula degeneration by optical means. For reasons of simplicity only the basic elements of the patients eye one are included in the figure, which are retina 2 and lens 3. On retina 2 an image is formed which is originated by optical radiation entering the eye being imaged basically by lens 3. For successful laser treatment contact lens 4 is placed at the cornea of the patients eye which minimizes possible eye movements and enables the laser radiation to enter the eye with out damaging the cornea and with enhanced imaging properties. Also for reasons of simplicity the complex optical system present in contact lens 4 is not shown. In any case contact lens 4 has a certain refractive power as is well known in state of the art laser treatment of the retina. Several different kinds of radiation are imaged on retina 2. One is treatment laser radiation 5. This radiation is originated by laser system 14, preferably a diode laser and coupled into optical fiber 13 which has a well defined core diameter and numerical aperture. Optical fiber 13 is a preferred element, because it simplifies the device and helps to shape treatment radiation 5 to the desired "top-hat" form with very sharp rising and falling intensity profiles at the edges and a plateau like near constant intensity elsewhere. Radiation 5 emitting from the fiber end is collimated by an optical system and optionally imaged to obtain a desired beam profile. None of these optics is a necessity, in fact quite a number of possible systems with an arbitrary number of lenses or even without any lenses can be used according to the targeted problem.

Beam source 14 uses another feature: it contains an optical system which allows for coupling the radiation of a secondary light source into optical fiber 13. This secondary light source preferably has a different wavelength and typically provides a much lower optical power than the treatment source. This additional light source bears the advantage that the visibility and thus the viewing possibilities are enhanced drastically because, due to the retina's optical characteristics, the treatment beam is sometimes hard to observe. Using viewing sources at a different wavelength resolves this problem, because the wavelength can be chosen in order to obtain the maximum viewing quality. Optional viewing radiation 16 is preferably imaged via optical system 10 as is treatment beam radiation 5 itself. For reasons of better visibility the secondary radiation is illustrated on a different optical path parallel to the primary radiation, though it can in general also take the same path depending on the optics.

Both types of radiation pass through beam adjustment device 12. The secondary radiation creates image 11 on the retina, which does not necessarily coincide with image 15 created by the treatment radiation itself. Never the less, since the radiation properties are known, it is possible to determine the treatment image from the secondary image.

The design of optical system 12 is a subject of the invention and is now described in detail. Common to all these embodiments is that adjustments by optical system 12 are not static ones but are variable to create variable images on retina 2 that have varying beam spot areas. It is common in laser based eye treatment methods to allow simultaneous viewing {inspection} of retina 2. Therefore, means of a slit-lamp are included in the device. In its simplest form, a slit lamp consists of light source 8 with a collimating optical system generating illumination radiation 7 with suitable optical characteristics. Mirror 9 is located at 45 degree with respect to the optical axis. The purpose of mirror 9 is to image the illumination into the eye. The illuminated area can be viewed along mirror 9 with back propagating image radiation 17 passing the slit of mirror 9 and entering optical system 18 fulfilling imaging purposes. Radiation 7 is chosen such, that it can pass through dichroic mirror 6 which is chosen highly reflective for treatment radiation 5 and optional secondary radiation 16, but not totally reflective, hence small parts of both, the treatment radiation 5 and secondary radiation 16 returning from retina 2 can pass through the mirror and contribute to the viewing means. Additional filters 19 can be optionally included in the path of viewing radiation 17 in order to enhance the quality or observing selectively only the result of one kind of radiation. Beam splitting means 20 is placed in the general optical system behind primary optics 18. A part of the radiation is mirrored into first secondary optical system 23 which creates an image on the detector area of digital image generation means 24, preferably a CCD camera. Another set of filters 19 can be applied in the path. The other part contributes via secondary optics 21 to a direct viewing by the operator, preferably a physician, via ocular 22.

As described earlier, the state of the art suffers from several deficiencies which basically originate from the fact that the area of the treatment zone cannot be determined accurately and thus all treatment beam spot size variation methods are rudimentary and produce an error up to 600%.

Figure 2:
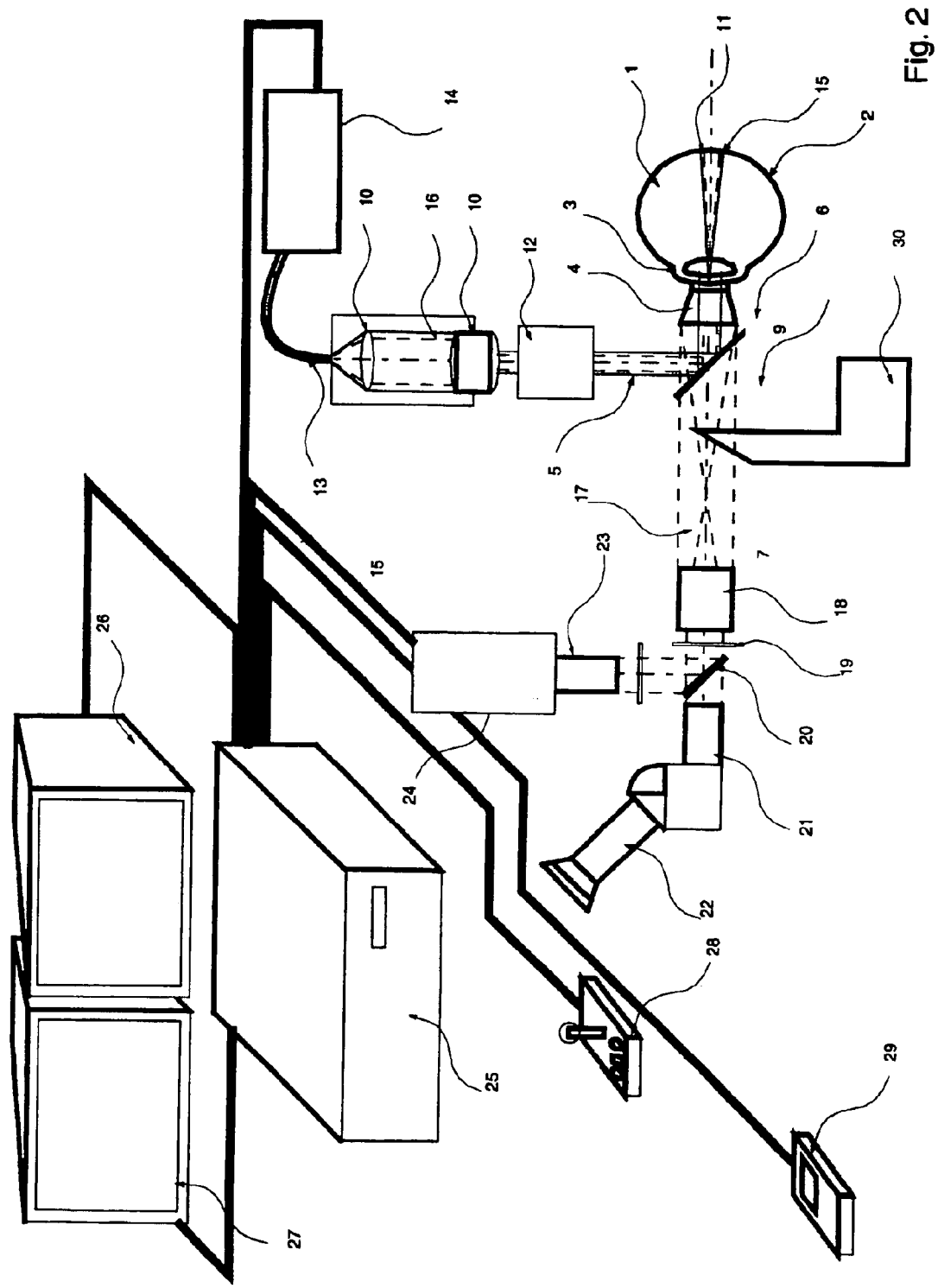
FIG. 2 illustrates integration of digital image processing means into a device for fundus treatment.

One significant innovation being subject of the invention has already been mentioned above: beam area generation means 10 are of a more sophisticated nature than in the prior art. FIG. 2 shows more elements that are part of the device to allow highly accurate treatment of the fundus of an eye. A central processing unit, preferably a PC in a desktop or an embedded form is used to control the incoming data from viewing devices 24 and to control the beam area generating variable optical system 12 accordingly. One or more display units 27 are connected to processing unit 25 to display the viewing data, external data and to perform operations in order to optimize the treatment procedure. To minimize the error in the treatment mentioned above, the device is such, that in several steps the treatment area is first determined in a relative way concerning the optical system being responsible for imaging the treatment beam to the retina and then the beam spot area is adjusted in the same relative way. This avoids a large source of error in the prior art, because the operator takes the treatment area from an image generated with fluorescence generated under different conditions, than present in the laser treatment device and in particular not very well known. To overcome this, a digital image using slit-lamp device 9 and digital image generation means 24 is taken. Further, another digital image is taken with the retina irradiated preferably by secondary light 16 with the optical system being responsible for setting up the treatment beam area on the retina in a pre-determined basic position. Alternatively, the treatment beam light can itself can be used, but at significantly lower radiation power. However, due to reasons of visibility explained above, the use of a secondary light source is preferred. From this image the spot size of treatment beam 5 can be precisely calculated in relative coordinates to the slit lamp generated image. Further, a digital image without treatment radiation or secondary radiation is taken at near equal time, meaning that the image is taken within a time interval short enough to assure, that the eye did not move. Alternatively a true equal time image can be taken using either digital image filtering means or using real filters and more than one digital image recording device. From this image the treatment zone may be determined with sufficient accuracy. If so, the operator marks the treatment zone with a simple software tool and the computer calculates the accurate size and coordinates. Applying a simple method, the operator can then use this data to manually adjust the beam area spot size with suitable optical system 12, which may be guided by electronic aids such as acoustical or optical signals. An even more accurate method is to have central processing unit 25 control optical system 10. The treatment beam parameters are also provided by central processing unit 25. The operator can now use manual positioning means 28 to locate the beam spot area center to a predetermined position within the treatment zone, preferably the center or one of the edges. As in the prior art, he can stop and start the treatment beam with a second external control, preferably a foot-piece, and simultaneously inspect the fundus in order to decide, if the treatment area and the treatment beam are aligned or if this alignment has been disturbed by eye-movement. A significant difference and advantage over the state of the art is, that the viewing can also be done via the digital image generated in real-time and illustrated on display unit 27. Digital image processing can enhance the image quality, and electronic image detection means 24 is more specifically sensitive to the applied wavelengths.

Another subject of the invention is to align the image generated by the slit-lamp means to a diagnostic image generated by means of fluorescence angiography. Slit lamp generated images are generally of medium quality and, depending on the status of the disease and the specific eyeball, the treatment zone can hardly be seen or may not be determined with sufficiently high accuracy. Therefore a digital angiography image is loaded onto central processing means 25 and displayed on display device 27. As before, simultaneously or quasi simultaneously a slit lamp image is taken with and without the treatment beam spot and also displayed for the operator. From a minimum of two characteristic points like blood vessel crossings which may be marked by the operator himself, the central processing unit aligns the two images, since they are in general of different form, because the optics or the eye position may vary. The operator further marks the treatment zone in the angiography image, which can be done with high accuracy. These coordinates are then calculated back to coordinates of the slit lamp picture and the system is able to calculate how, optical system 12 responsible for the treatment beam spot generation must be adjusted in order to achieve high overlap accuracy. As described above, the adjustment can be performed manually with possibly electronic aids or fully automatically. In a preferred embodiment the complete adjustment, including the positioning of the beam spot to the treatment area, the treatment process and the treatment control is performed automatically by the central processing unit on the basis of a real-time viewing of the retina with the digital image processing means.

Figure 3:
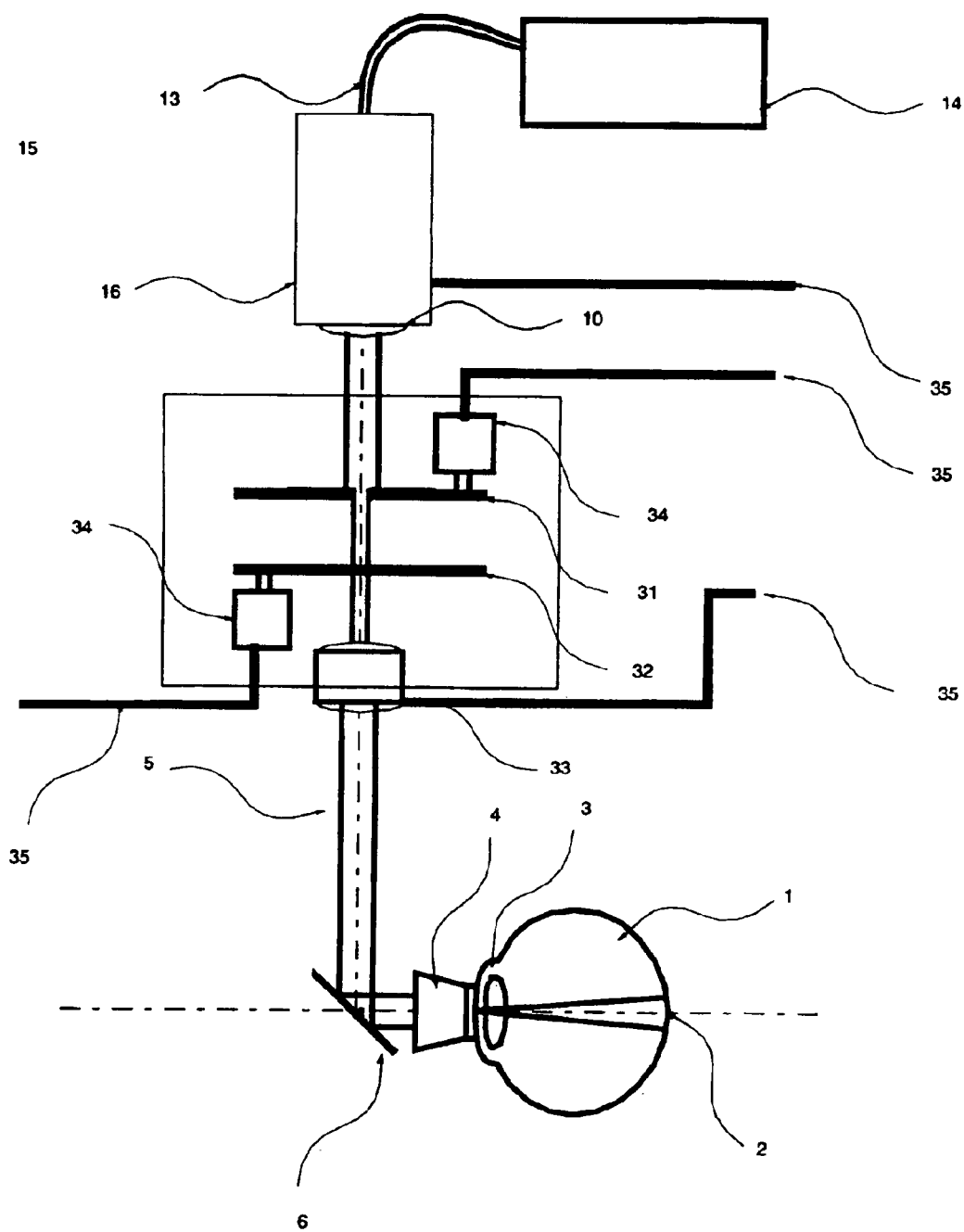
FIG. 3 shows a variable aperture imaging method to obtain a sharp edged intensity profile of variable beam spot area on a retina.

FIG. 3 illustrates a preferred embodiment for optical device 12 which is responsible for the generation of the treatment beam area The treatment beam is produced by primary beam source 14 and preferably coupled into optical fiber or light guide 13 to be shaped to the desired top hat intensity profile and to be transported with simple means from primary beam source 14 to the treatment device allowing the beam source to be spatially separated, which is of particular importance for laser sources due to safety requirements. From there primary radiation 5 illuminates aperture 31. The radiation can illuminate aperture 31 either in a direct way or be imaged via suitable optical elements, preferably forming a telescope, to produce a fixed spot on aperture 31. In particular, radiation 5 can be collimated optimally in order to minimize the divergence angle. Aperture 31 cuts a defined section from said beam. This cut has, apart from diffraction limits, a sharp intensity edges, what is of great advantage to the treatment process, because it assures that all parts of the treatment zone are irradiated with the same energy. Aperture 31 is adjustable whether via mechanical means like micrometer screws to be moved via the operator directly or via electromechanical means 34 like step motors or piezo actuators. Means 34 can be controlled via the operator directly with suitable control devices or via central processing unit 25 they are connected with via interface lines 35. More than one aperture may be included within the setup, one of which 32 is illustrated in FIG. 3. This apertures can be controlled in the same manner as the primary aperture and serve for various purposes. One is the generation of a two dimensional irradiation surface on the retina which is of higher complexity than the simple circle, that would be the best choice for single aperture 31. For example the combination of a circular aperture with a slit aperture allows near-oval irradiation spots or two slit apertures allow rectangular forms. In a preferred embodiment the whole aperture unit is exchangeable, hence the operator can choose a certain combination in order to adjust the image to the treatment beam area which is visible from the diagnostic fluorescence angiography. Common to the optical system is as already mentioned the basic position. For the case of the aperture based solution to the adjustment of beam spot size to treatment zone size basic position of electromechanical dislocation means 34 is directly related to a certain basic aperture size of apertures 31 and 32 or eventually more. This size is first illuminated with secondary beam 16 and the radiation passing the aperture propagates to the eyepiece for, or is optionally imaged via optical system 33. The image of the aperture on the retina is then recorded and digitized. This digital image is one of the basic images mentioned above to perform the calibration. Therefore, secondary beam 16 must be coupled into the propagation path of primary radiation 5. This is done in a unique and well known way in order to have a well defined system of coordinates to compute from secondary beam retina image 11 to primary beam shape 15 and its spot size, in a preferred embodiment secondary beam 16 is already coupled to optical fiber 13 together with the treatment beam. The operator can then use primary beam 5 to chose the exact position of the treatment zone and start the process. This is performed as described above utilizing the means illustrated in FIG. 2.

Figure 4:
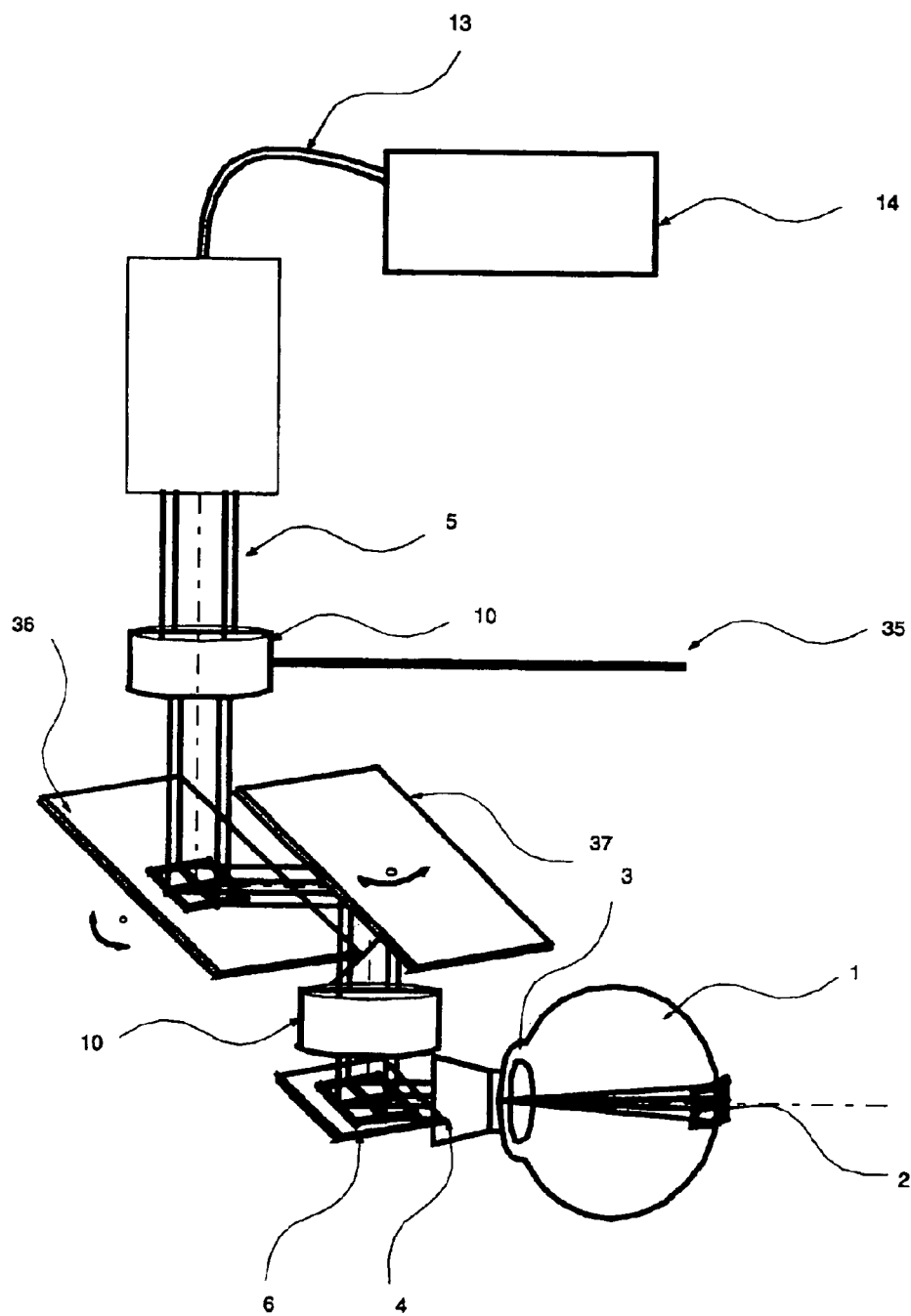
FIG. 4 illustrates implementation of a scanner system with suitable optical imaging means in order to obtain a sharp edged intensity profile of arbitrary beam spot area on a retina.

FIG. 4 illustrates a more advanced system for the generation of the treatment beam area on the retina. State of the art methods suffer from the deficiency that they produce round spots since optical fibers, laser profiles or lamp emitted radiation generally produce round spots. These spots are then shaped and imaged to the retina The new method illustrated in FIG. 3 and described above already is a significant innovation over the state of the art, since it allows other than round profiles. Additionally, the treatment beam is kept at small sizes and thus there is no longer a requirement for a rectangular top hat intensity profile. However, the treatment zone usually has a much more complicated form. In the prior art, the treatment zone could not be determined with sufficient accuracy, hence there was no need for the generation of an accurate treatment beam area. By the methods of this invention the treatment zone becomes well known, hence the mechanisms to illuminate said treatment zone can be enhanced in the same degree. FIG. 4 basically consists of the components described above, but adjusting optical system 12 is embodied as a scanning device. In its most basic form a scanner contains two movable mirrors 36 and 37 positioned in an orthogonal way. The angle relative to the optical axis of each mirror is adjustable in one dimension, hence according to their orthogonal position by independent angle variation the beam can be positioned to an arbitrary position on a two dimensional surface. This surface can further be imaged and such an imaging is performed via contact lens 4 and the eye-lens onto the retina. Source 14 can be collimated, optionally be expanded to the desired diameter with suitable optical system 10 and then be directly imaged by the scanning means.

The eye lens and the original beam diameter hitting the eye lens are responsible for the size of the beam spot on the retina, on which the beam delivered by the treatment beam spot is dependent on the beam diameter and divergence angle when it hits the contact lens and on the contact lens itself. By varying the contact lens and the beam properties by means of adjustable optical system 10 the beam spot on the retina can be varied accordingly. For use with a scanner the beam is of relatively low power and small size. If the scan velocity is chosen sufficiently large, each spot on the treatment zone is impinged by a sufficiently large number of photons for an optimal treatment process.

To generate a true image of the treatment zone determined by use of the methods described above, two ways can be followed. The first consists in the generation of a rectangular image and switching the primary beam source on and off sufficiently fast, hence simply no intensity is emitted if the scanner positions a point out of the treatment zone and the laser is on if the scanner positions a point on the treatment zone. Hence even non connected treatment zones can be mapped accurately.

The second method is to operate the scanner in an asynchronous mode with interruption. Mirrors 36 and 37 do not just map a rectangle, they rather map the concrete form of the treatment zone. This enhances the scanning efficiency and lowers the requirements to the switching velocity of primary beam source 14. However, the requirements to the scanner deflection properties rise.

Scanner deflection can be implemented by various methods, two commons are to include galvano-metric driven mirrors and piezo actuator driven mirrors.

Principally, instead of two orthogonal one dimensional deflecting mirrors a single two dimensional deflecting mirror can be used. A scanner system can be even of higher complexity. Today, micro-mirror devices are commercially available, for example by Texas Instruments, Inc. of Houston, Tex. which consist of a two dimensional array of micro mirrors. These devices are able to produce pixel based 2-dimensional image structure which can be used for display technologies, in micro machining and for applications in medicine. A device of this type is included as the basic element of adjusting optical system 12, optionally combined with suitable optical elements to create optical images which fulfill all the requirements given by the micro-mirror device and the treatment zone. The micro-mirror device is directly controlled by central processing unit 25. The image created directly propagates via the optics and contact lens 4 to the retina.

An equivalent effect to the micro mirror method can be achieved using liquid crystal devices and polarizers, similar to the use of liquid crystal devices in printing, display and lithography applications. Adjusting optical system 12 then contains an optical setup which is a liquid crystal modulation device which allows to generate an image formed by a sufficiently large number pixels of that matches the treatment zone. It is obvious, that any image generation means can be included in a treatment setup to generate the treatment zone illumination beam area.

The optics further can be positioned externally by the operator for example using positioning means 28. In particular, said positioning to treatment zone is enhanced by using the secondary beam source as aiming beam and using the digital image recording and processing means described above. The switching the laser on and off is performed in an The use of a scanner system as described only makes sense if it is operated with a sufficiently fast driving electronics and controlled by a computer based system. The inclusion of a system of this type and the connection of all variable elements to the central processing unit is also a subject of the invention.

Figure 5:
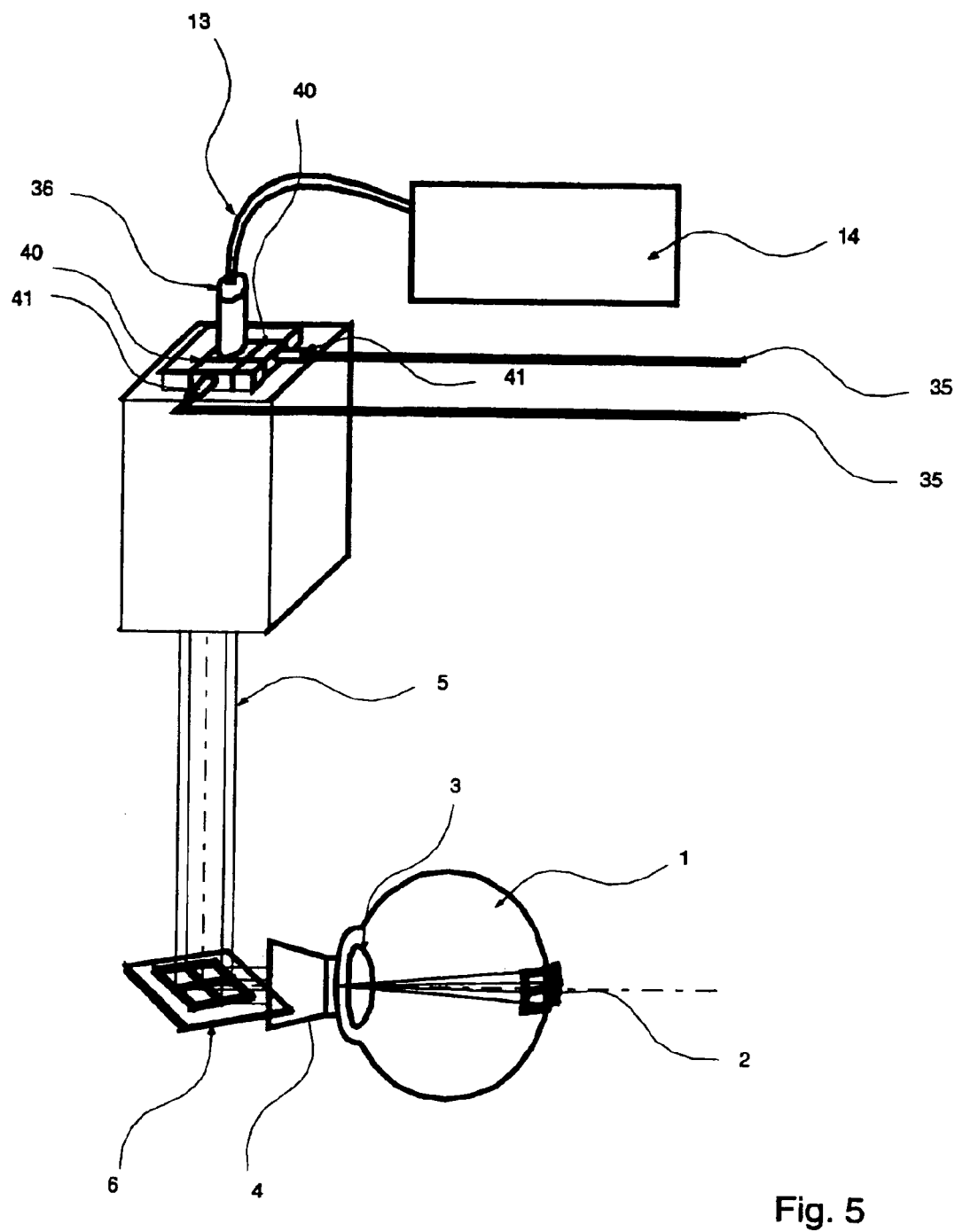
FIG. 5 illustrates implementation of an optical system including a two dimensional movable beam source in the device in order to obtain a sharp edged intensity profile of arbitrary beam spot area on a retina.

FIG. 4 shows another innovative method for the generation of variable image on the retina. From the point of the operator and the patient, this method provides an equivalent interface for the treatment itself and the result will also be comparable to the results obtained by using scanner methods. In fact the scanning facility is maintained, but in this case secondary light source 16 itself, if directly included in the treatment setup, or the emitting end of fiber 13 if the beam source is external and it's produced radiation is transported to the treatment device by fiber 13, is moved along a special path. This movement can, as with the scanning method before, follow a complicated path directly or follow a rasterized rectangle. Primary light source 14 is switched according to the treatment size image requirements. To generate the movement of, for example, the fiber end, a two dimensional scanning unit can be constructed either mechanically, electromechanically by the application of piezo actuators or by a combination of these. In FIG. 5, fiber 13 is connected to mount 36. Mount 36 is fixed on two dimensional displacement unit 40. Actuators 41, preferably piezo actuators, cause the appropriate movements and are connected with central processing unit 25 by connection lines 35. Since aiming beam 16 produced by the fiber is preferably transported by said fiber it follows the same contour as treatment beam 5 and can thus be still used for all purposes mentioned above. The optical system images the plane, in which the fiber end moves to the retina. Optionally, the optical system can be varied automatically by central control unit 25 or be exchangeable in order to achieve different imaging relations.

Figure 6:
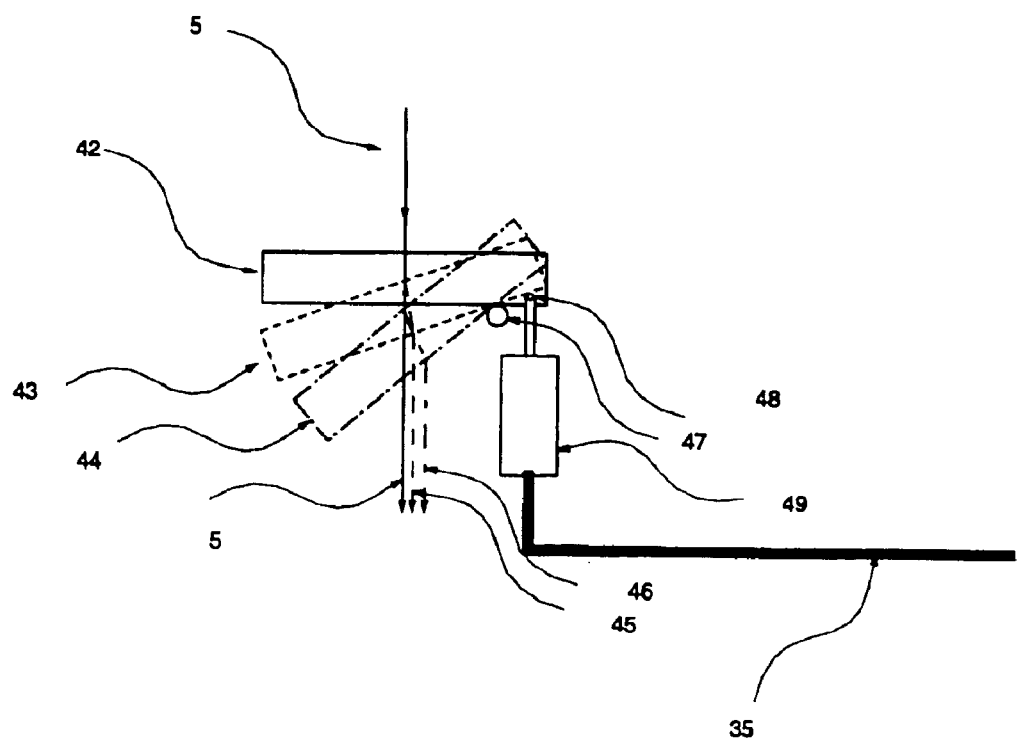
FIG. 6 contains an alternative device for the displacement of the laser beam to treat a two dimensional treatment area.

FIG. 6 illustrates another element which can be implemented in the optical path to achieve the desired beam displacement. Incoming treatment beam 5 passes parallel plate 42 optionally coated dielectrically in order to minimize losses. This plate is mounted movably with one reference point on cylinder 47. Relative to this reference point the plate can now be rotated for a certain angle by actuator 49, which can be a simple stepper or, preferably, a piezo actuator, which is in suitable contact with parallel plate 42. In particular it must allow a certain linear movement of the actuating point Because of this angle, incoming beam 5 is displaced by a certain distance hence outgoing beams 45 and 46 are parallel the incoming beam, but displaced by different distances according to the angle at which the plate is positioned within the beam. If the plate is in the position marked by feature 43 it creates a smaller displacement in particular beam 45, than if it is in the position marked by feature 44, where displaced beam 46 is uniquely given by a mathematical relation between the displacement and the angle and can hence be controlled accurately. The two dimensional displacement can be obtained either by the use of two orthogonal devices each producing a displacement in one direction or a single plate, which has one fixed reference point and two orthogonal variable points. For this displacement unit all optical and electronic features described above can be used.

Figure 7:
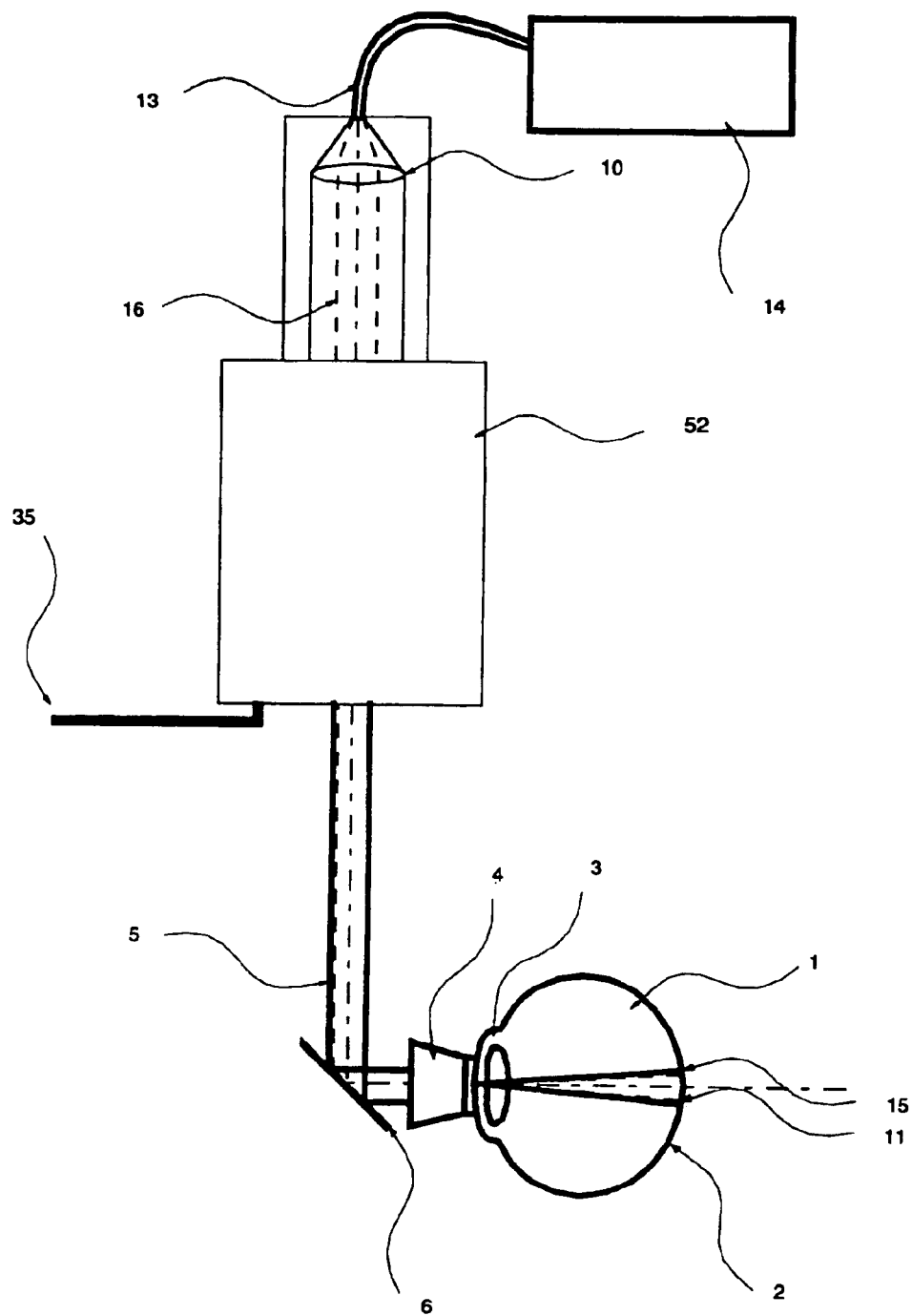
FIG. 7 illustrates the use of a telescope to vary beam spot size into the device.

FIG. 7 illustrates another embodiment of treatment optics. Primary light source 14 creates treatment radiation 5, which is preferably coupled into optical fiber 13 and transported to the treatment device, together with secondary radiation 17 which serves as aiming beam and preferably has a different wavelength. The output 5 and 16 from fiber 13 is preferably collimated by optical system 10 and then coupled into optical system 52, which plays the role of adjusting optical system 12 in prior embodiments. System 52 consists of the optical module of a commercial video camcorder, which is available as a component, as for example the Sony ELI Series. In their original application these modules are intended to generate images on a camera chip for different object distances, which is basically equivalent to the purpose required for the treatment of the fundus of an eye. The optical states of module 52 can be varied electronically through interface 35 and central processing unit (not shown), which is preferably a PC. The reference image used for the calibration of the angiography to the native fundus image is recorded at a fixed position of the video module and with the data obtained from the image calibration. The correct state is chosen in order to generate a well defined treatment spot on the treatment zone. The principal treatment features are equivalent to the other embodiments described above. This method can in particular be combined with the aperture method which enhances the performance because it allows other than round profiles, the aperture creates top hat intensity structures if desired and operated far from the diffraction limit and the process can be implemented electronically and thus be controlled completely by a central processing means simply.

Having described preferred embodiments of the invention with reference to accompanying drawings it is to be understood that the invention is not limited to those precise embodiments, and that various changes and modifications may be effected therein by one skilled in the art without departing from the scope or the spirit of the invention as defined in the appended claims.

What is claimed is:

1. An improved, accurate method of treatment of an eye's fundus, using a treatment optical system with a slit lamp assembly and fluorescence angiography, comprising the steps of:

generating a treatment beam from a primary light source;

creating a native digital image of an eye's retina using said treatment optical system and said primary light source;

generating a secondary beam using a secondary light source;

generating a digital reference image on an eye's retina at a predetermined position using said treatment optical system and said secondary light source;

wherein said secondary light source operates at a different wavelength from said primary light source;

controlling and processing said digital reference image and said native digital image by at least one computer to accurately determine a treatment zone;

marking uniquely said treatment zone onto a corresponding region of said native digital image, wherein said treatment zone is marked by means of a software tool;

adjusting said treatment beam and said treatment optical system to have said treatment beam cover said treatment zone; and irradiating said treatment zone.

2. A method of treatment of an eye's fundus according to claim 1, wherein said adjusting is accomplished by one of the following group of methods: manually completing by an operator, assisting with electronic means, preferably with optical or acoustical signals, and completing fully automatically.

3. A method of treatment of an eye's fundus according to claim 1, further comprising the steps of:

aligning said native digital fundus image with said image of said treatment zone by applying suitable mathematical algorithms to transform between coordinate systems for these two images;

wherein said aligning is accomplished by one of the following methods: an automatically operating pattern recognition scheme, and manually marking at least two reference points in each image;

illuminating and imaging at least one variable aperture with an optical system onto said treatment zone on said retina; and imaging said treatment beam onto said variable aperture and onto said retina to create various polygonal shapes.

4. A method of treatment of an eye's fundus according to claim 3, further comprising the step of:

sequentially applying at least two apertures having different shapes to generate said image on said retina in more complicated geometrical shapes than polygonal shapes.

5. A method of treatment of an eye's fundus according to claim 4, wherein said apertures are varied independently of each other and can be adjusted manually, semi-automatically or automatically to a desired size.

6. A method of treatment of an eye's fundus according to claim 3, further comprising the step of:

further adjusting of said optical system imaging said treatment beam by scanning with at least two variable, linear, orthogonal-arranged devices and using an automatic primary beam power switch to create an arbitrary-shaped two dimensional region substantially equivalent to said treatment zone.

7. A method of treatment of an eye's fundus according to claim 4, wherein said scanning of said treatment beam over said treatment zone irradiates each point in the treatment zone for a predetermined period of time.

8. A method of treatment of an eye's fundus according to claim 6, wherein said further adjusting is accomplished by one of the following group of methods:

manually completing by an operator, assisting with electronic means, preferably with optical or acoustical signals, and completing fully automatically.

9. A method of treatment of an eye's fundus according to claim 1, wherein said secondary light source operates preferably at a green wavelength; and wherein said secondary light source produces a geometrical image other than a spot and preferably said geometrical image contains at least one of the following group of shapes: a ring shape, and a cruciform shape.

10. A method of treatment of an eye's fundus according to claim 3, wherein said imaging of said treatment beam is positioned manually on said retina, preferably being positioned there by at least one secondary target spot and wherein said native digital image of the fundus is generated in real time, and said position of said treatment spot area is determined electronically and transformed into said coordinate system of said diagnostic fluorescence angiography and displayed thereon.

11. A method of treatment of an eye's fundus according to claim 10, wherein in real time said position of said treatment zone is determined and said treatment light source is appropriately switched on and off, wherein said native image of said fundus containing said spot of said treatment beam and said image generated diagnostically by fluorescence angiography means are digitally processed, superimposed and presented on a display device, and wherein in real time said position of said treatment zone is determined and said treatment beam spot is positioned in real time according to said treatment beam spot position.

12. A method of treatment of an eye's fundus according to claim 11, wherein in real time a position of a point on said retina or said cornea, rather than on said treatment zone, is determined and said position of aid treatment zone is calculated therefrom.

13. A method of treatment of an eye's fundus according to claim 1, further comprising the step of:

varying power of said treatment beam generated by said primary light source to allow for optical losses occurring along said optical path in order to keep constant power on said retina.

* * * * *